United States Patent
Okano et al.

(10) Patent No.: US 9,114,192 B2
(45) Date of Patent: Aug. 25, 2015

(54) CULTURED PERIODONTAL LIGAMENT CELL SHEET, PROCESS FOR PRODUCING THE SAME AND METHOD OF USE THEREOF

(75) Inventors: Teruo Okano, Ichikawa (JP); Masateru Hasegawa, Tokyo (JP); Masayuki Yamato, Tokyo (JP); Akihiko Kikuchi, Tokyo (JP); Isao Ishikawa, Narashino (JP)

(73) Assignee: CELLSEED INC., Tokyo (JP)

( * ) Notice: Subject to any disclaimer, the term of this patent is extended or adjusted under 35 U.S.C. 154(b) by 1810 days.

(21) Appl. No.: 11/587,427

(22) PCT Filed: Apr. 25, 2005

(86) PCT No.: PCT/JP2005/007853
§ 371 (c)(1),
(2), (4) Date: Aug. 1, 2007

(87) PCT Pub. No.: WO2005/103233
PCT Pub. Date: Nov. 3, 2005

(65) Prior Publication Data
US 2008/0118474 A1    May 22, 2008

(30) Foreign Application Priority Data
Apr. 25, 2004  (JP) .................................. 2004-158414

(51) Int. Cl.
*A61K 6/00*       (2006.01)
*A61L 27/38*      (2006.01)
(Continued)

(52) U.S. Cl.
CPC ............. *A61L 27/3886* (2013.01); *A61K 35/32* (2013.01); *A61L 27/3804* (2013.01);
(Continued)

(58) Field of Classification Search
None
See application file for complete search history.

(56) References Cited

U.S. PATENT DOCUMENTS

| 5,032,445 A * | 7/1991 | Scantlebury et al. ......... 428/158 |
| 2004/0009566 A1 | 1/2004 | Okano et al. |

(Continued)

FOREIGN PATENT DOCUMENTS

| EP | 1 302 535 A1 | 4/2003 |
| JP | 2002-262862 | 9/2002 |

(Continued)

OTHER PUBLICATIONS

Yamasaki, A. and Pinero, G.J., "An ultrastructural study of human epithelial rests of malassez maintained in a differentiated state in vitro" Arch. Oral Biol., 1989, 34(6), pp. 443-451.*

(Continued)

*Primary Examiner* — Rosanne Kosson
*Assistant Examiner* — Aaron J Kosar
(74) *Attorney, Agent, or Firm* — Nixon & Vanderhye PC

(57) ABSTRACT

A cultured periodontal membrane cell sheet, produced through a process comprising culturing cells on a cell culture support composed of a base material having its surface coated with a temperature-responsive polymer of 0°C to 80°C upper limit or lower limit critical dissolution temperature in water under specified conditions, (1) regulating the temperature of culture fluid to temperature≥the upper limit critical dissolution temperature or≤the lower limit critical dissolution temperature, (2) causing a cultured periodontal membrane cell sheet resulting from the culturing to adhere to a carrier, and (3) detaching the sheet together with the carrier. This cultured periodontal membrane cell sheet has a syndesmotic microstructure, exhibiting extremely high bioadherence to the surface of dental root, and realizes high-density transplant of target cells and positive reconstruction of periodontal tissue. Moreover, through laminating of cell sheets to be transplanted and donating of three-dimensional polarity, highly efficient reconstruction of attachment apparatus can be accomplished, and clinical application thereof to moderate periodontitis, severe periodontitis, gingival recession, etc. is highly promising.

20 Claims, 6 Drawing Sheets

(51) Int. Cl.
*A61K 35/32* (2015.01)
*C12N 5/077* (2010.01)
*A61C 8/02* (2006.01)

(52) U.S. Cl.
CPC ............ *A61L 27/3865* (2013.01); *C12N 5/066* (2013.01); *A61C 8/0006* (2013.01); *C12N 2502/097* (2013.01); *C12N 2502/1311* (2013.01); *C12N 2513/00* (2013.01); *C12N 2539/10* (2013.01)

(56) References Cited

U.S. PATENT DOCUMENTS

| | | | |
|---|---|---|---|
| 2004/0028657 | A1 | 2/2004 | Okano et al. |
| 2006/0234377 | A1 | 10/2006 | Okano et al. |
| 2006/0240400 | A1 | 10/2006 | Yamato et al. |
| 2006/0240552 | A1 | 10/2006 | Yamato et al. |
| 2007/0092492 | A1 | 4/2007 | Matsuda et al. |
| 2007/0148137 | A1 | 6/2007 | Okano et al. |
| 2008/0131476 | A1 | 6/2008 | Kanzaki et al. |
| 2008/0226692 | A1 | 9/2008 | Sato et al. |
| 2008/0289052 | A1 | 11/2008 | Okano et al. |
| 2011/0229962 | A1 | 9/2011 | Mizutani et al. |
| 2012/0107930 | A1 | 5/2012 | Sasaki et al. |
| 2012/0156781 | A1 | 6/2012 | Takahashi et al. |
| 2012/0210451 | A1 | 8/2012 | Shimizu et al. |

FOREIGN PATENT DOCUMENTS

| | | | |
|---|---|---|---|
| JP | 2002-262862 A | | 9/2002 |
| JP | 2003-038170 | | 2/2003 |
| JP | 2003-190273 A | | 7/2003 |
| JP | 2004-000497 | | 1/2004 |
| WO | 02/10349 | | 2/2002 |
| WO | 02/061052 | A2 | 8/2002 |
| WO | 03/052084 | A2 | 6/2003 |

OTHER PUBLICATIONS

Bloom and Fawcett, "Teeth" A Textbook of Histology, 12th ed. Chapman, 1986, chapter 24, pp. 578-592.*
International Search Report of PCT/JP2005/007853, mailed Jun. 28, 2005.
Hasegawa et al; "Koku Gekagaku Shishu Soshiki no Sasei Iryo", Igaku no Ayumi (2003), vol. 207, No. 12/13, pp. 1011-1012.
Nagai et al; A Method of Cell-Sheet Preparation Using Collagenase Digestion of SalmonAtelocollagen Fibrillar Gel J. Biosci. Bioeng. (Dec. 25, 2004), vol. 98, No. 6, pp. 493-496.
Hasegawa et al; Human periodontal ligament cell sheets can regenerate periodontal ligament tissue in an athymic rat model, Tissue Eng. (Mar. 2005), vol. 11, No. 3-4, pp. 469-478.
Akizuki et al; Application of periodontal ligament cell sheet for periodontal ligament cell sheet for periodontal regeneration: a pilot study in beagle dogs, J. Periodontal Res. (Jun. 2005), vol. 40, No. 3, pp. 245-251.
Hasegawa et al. "Method for regenerating periodontal tissues based on cell sheet engineering" Kokubyou Gakkai Gakujyutsu Takai Kouenn Shouroku, abstract presented at 68th Academic Meeting of the Stomatological Society, pp. 44-45 (2003) and complete English translation.
Ishikawa et al. Quintessence, vol. 22, No. 4, pp. 196-199 (2003) and partial English translation.
Hasegawa et al. "Koku Gekagaku Shishu Soshiki no Sasei Iryo" Igaku no Ayumi 207:1011-1012 (2003).

* cited by examiner

Azan Staining          H-E Staining

One Week After Transplantation

Four Weeks After Transplantation

CULTURED PERIODONTAL LIGAMENT CELL SHEET, PROCESS FOR PRODUCING THE SAME AND METHOD OF USE THEREOF

This application is the US national phase of international application PCT/JP2005/007853, filed 25 Apr. 2005, which designated the U.S. and claims priority of JP 2004-158414, filed 25 Apr. 2004, the entire contents of each of which are hereby incorporated by reference.

TECHNICAL FIELD

The present invention relates to a cultured periodontal ligament cell sheet, a process for producing the same and a therapeutic method utilizing the same in the field such as biology and medicine

BACKGROUND ART

Japan has reached a society composed largely of elderly people and the average life span is highest in the world. The hope of people is attaching importance to the quality of life (QOL) rather than to mere life prolongation, and speaking and eating are important functions to lead to the be-all of particularly the elderly people's existence and in that sense, health maintenance of organs of mastication including the preservation of teeth can be said an important factor in controlling QOL. Mastication is an inevitable function of ingestion, and furthermore according to the recent study of the system of mastication, it is being clarified that mastication affects various systemic functions such as urging of development and activation of mind/nerves by stimulating brain cells, enhancement of immune functions and further inhibition of obesity. Accordingly, the decline of the function of mastication due to the loss of teeth leads to a possibility of accelerating the way to dementia and causing life style related diseases or the like. At present, with the middle-aged and the elderly of 35 to 65 ages, the ratio of population affected by periodontitis is more than 80% and the demand of the people is high in treating periodontitis and its contents are varied. Many associated factors complicatedly have a part in the onset and progression of periodontitis, and the preventive treatment centering on the oral cavity cleaning which has been performed heretofore cannot solve periotontitis. People who unfortunately get periodontitis and are treated mostly demand functional recovery and an aesthetic improvement and at this stage, the treating method centering on the non-regenerative treating method which has been performed heretofore for these demands can be said insufficient and a revolutionary treating method which can regenerate lost periodontal tissues is demanded.

Teeth erupt through the epithelium and are exposed into the oral cavity and lose continuity on the boundary between the teeth and the gingiva and are in a very specific environment in a living body. The teeth and the gingival are constituted of "epithelium adherence" and "connective tissue adherence. As to the former, the epithelium called as junctional epithelium adheres to the dental surface (enamel) through the hemidesmosome and the basal plate. The latter is constituted of the periodontal ligament, and while collagen tissues are mineralized in the cementum of the dental root surface, the tissues anchors into the alveolar bone while being also mineralized to migrate into the gingival tissue, and accordingly teeth are firmly bonded to the alveolar bone and the gingiva.

Periodontitis is an inflammatory disease in the periodontal tissue caused by plaque bacteria and classified into "periodontitis" and "gingivitis". The inflammation limited to the gingiva is called as "gingivitis" and the inflammation leading to the periodontal ligament and the alveolar bone to destruct the adhesion by the periodontal ligament is called as "periodontitis". In general, the gingivitis proceeds to periodontitis to result in the formation of a pocket (a groove) in the periphery of teeth. With the pocket deepened, the plaque bacteria in the pocket proliferate to advance the inflammation to the depth. The localized restoring factor as called occlusal traumatism which is found when somatic modified factors (a drug, a blood disease, an immunological disease, nutritional state, stress, fatigue, smoking and the like) are involved and, in addition, the mechanical load to teeth such as grinding of teeth becomes excessive to worsen the inflammation. According to the case of disease seized with periodontitis to highly advance tissue destruction, once lost periodontal tissues cannot be restored in the original form and functions even when tooth extraction is avoided and after treatment, a remarkable functional/aesthetic damage remains to come to a big factor to lower QOL of the patient.

The resorption of the alveolar bone is one of the states of disease characteristic to periodontitis, and the simultaneously occurring loss of the dental root cementum and the periodontal ligament (periodontal ligament) is the essential state of disease. The periodontal ligament indicates a syndesmotic structure as its name shows and suspends teeth in the socket of the alveolar bone through the cementum of the dental root surface to play a role of cushioning a strong bite pressure and is rich in vascular components and has a high metabolic activity to play an important role of maintaining the homeostasis of periodontal tissues. In spite of many studies to aim at the regeneration of periodontal tissues over nearly half a century, an appropriate treatment method has not been established yet because simultaneous regeneration of both the alveolar bone and the periodontal ligament tissue is very difficult. It is clarified that without the regeneration of the periodontal ligament, intrusion of the oral cavity epithelium into a defect and bony ankylosis of the dental root are caused to be healed in a biologically unstable state, and they come to the cause of inviting the recurrence of periodontitis and the deciduation of tooth In order to treat this periodontitis, scaling/root planing S/RP) is being performed. This is an operation method which comes to the basis of the treatment of periodontitis and comprises mechanically removing infectious tissues at the affected site of periodontitis, mainly removing the cementum of the dental root surface, the periodontal ligament and the gingival tissue which are contaminated by bacterial infection with the use of specific equipment and attaching the peripheral tissue in an easy adherent form to the dental root surface to expect spontaneous cure. The healing form is mainly epithelial adherence formed by the epithelium which is allowed to proceed and proliferate on the dental root surface to be treated. This method does not require a surgical treatment and enables the treatment without anesthesia or by local infiltration anesthesia alone and is a necessary and sufficient treating method if the site to be treated has no aesthetic and functional problem. However, in a case of a destructed alveolar bone in an advanced stage of periodontitis, when reinfection is presumed after treatment, this treating method alone is not sufficient. Further, at the site complicated in the shape of a tooth, this operation method tends to be difficult, and in this case a surgical treating method is applied. The site complicated in the shape of the tooth which cannot be treated by S/RP alone is provided with a surgical treatment which surgically forms a gingival flap to visually treat it. The healing form basically expects the same epithelial adherence as in S/RP.

Under these circumstances, the regenerative medicine technique for positively reconstructing periodontal tissues has been being actively studied. Several techniques are already utilized in the treatment and include, for example, excision of tooth, bone transplantation and mucous ligament transplantation. This alveolar bone transplantation is classified into bone autotransplantation, allotransplantation heterotranplantation and artificial bone transplantation. The bone autotransplantation is mainly performed and is a method of transplanting a bone segment collected from another site in the oral cavity into a bone defect. Further, a decalcified freeze-dried bone allotransplantation (DFDBA) is used in Western countries to get better clinical results. As the artificial bone, hydroxyapatite (HA) is used as a representative. The healing form has an aspect of effectively acting on the retention of blood clot in a defective site compared to S/RP alone, and it is thought that the conditions of inhibiting the intrusion of the epithelium and simultaneously enabling easy migration of the periodontal ligament cells can be provided but it is reported that the main healing form in animal experimentation mainly comes to epithelial adherence which does not cause the regeneration of neocementum and periodontal ligament. The bone autotransplantation has a smallest problem of antigenicity and infection and can be naturally easily accepted in the receptive part. Further, it has an advantage of expecting bone conductivity and bone inductiveness in bone transplant materials. However, it is very difficult to secure a necessary amount of transplant bones in bone autotransplantation. Further, the problem of antigenicty/infection remains in the bone allo- and hetero-transplantation, and there has been a problem that independently of the types of transplant materials, bony ankylosis of a tooth having a large bone defective site and a large area of a transplant bone in contact with the dental root surface is caused.

Between the late 1970's and 1980's, a research group in Scandinavia confirmed that the epithelial tissue and the gingival connective tissue are lacking in the regenerative capacity and the bone tissue causes bone ankylosis on the dental root surface and found that for the regeneration of periodontal ligament tissues, it is necessary for the cells derived from periodontal ligament tissues to be present in a defect, particularly on the dental root surface. It is the "guided tissue regeneration method" (GTR method) that was devised on the basis of this concept. This method enables the regeneration of periodontal ligament tissues by inhibiting the intrusion of the epithelial cell which has a high proliferation speed to early proceed to the defect with a biocompatible shielding ligament to simultaneously perform a space-making in the defect. At present, this method can most expect the regeneration of periodontal tissues and gets better results in the site showing a bone defective form easy in space making. However, this method had problems such that the clinical operation method was complicated; as to the site showing a complicated defective form, it was difficult to accurately place the biocompatible ligament on the dental root surface; the ligament had to be completely covered with a gingival flap during healing due to the standpoint of infection; and prognosis was easily affected by the operation method and the environment. Further, the biocompatible ligament is of absorptiveness and of nonabsorptiveness, and the use of the former required reoperation for removing the ligament and the use of the latter did not require reoperation but a problem of its strength for performing space making remained. Since the cell migration from the residual periodontal ligament is expected, the amount reproduced is limited and additionally, viewed from the retention of the ligament, an applied case is limited to part of the vertical bone defect. In the diffuse chronic periodontitis widely seen in the middle-aged and the elderly, the main state of disease is horizontal bone resorption, and not a few cannot be coped with this GTR method.

Thus, even if periodontal ligament-derived cells are understood to be an indispensable factor to the regeneration of periodontal tissues, in the present situations, the conventional treatment methods including this GTR method only expect the cell migration from the residual tissues in spite of the application of a growth factor and are greatly affected by the defective form and the amount of the residual periodontal tissues to limit its indications. In highly damaged periodontal tissues, mere expectation of the migration of cells of a basis for regeneration from the residual peripheral tissues is not sufficient and the necessity to externally supply periodontal tissues is being clarified. The object of regenerative treatment in periodontal tissues places the focus on how to inhibit the healing by the epithelial adherence to acquire the connective tissue adherence by the periodontal ligament.

In recent years, several studies of aiming at the tissue regeneration by the cell transplantation method are reported. These studies are mostly to perform the injection transplantation of a three-dimensional matrix seeded with a single type of cells to a tissue defect but any of them has not yet realized an expected tissue reconstruction. The reason is thought to be the difficulty in the selection of a cell source and the control of the localization of cell differentiation in the tissue defect. The regeneration of periodontal tissues is inevitably accompanied by cementification on the dental root surface, and it is necessary that both the periodontal ligament of soft tissues and the cementum or the alveolar bone of hard tissues are simultaneously regenerated and functionally connected to each other. When these two types of tissues are formed with a time lag by the action of the precursor cell and the growth factor which are different and tissue-specific, the cell transplanting method in the regeneration of periodontal tissues must be more delicate. In other words, not that a single type of cells is merely injected to the defect undergone space-making and left to tissue differentiation in the living body but that it is necessary to regulate the site of arrangement of cells to arrange the cells at respective appropriate sites.

The cells necessary in this instance have been cultured on the surface of glass or the surface of a synthetic polymer having undergone various treatments. Various vessels made of a material such as polystyrene having undergone surface treatment such as γ-ray irradiation and silicone coating are popularized as cell culture vessels. The cultured/proliferated cells with the use of such cell culture vessels are detached/recovered from the surface of the vessels by treatment with a protease such as trypsin and a chemical. However, such defects have been pointed out that the recovery of the proliferated cell by providing the above described chemical treatment makes the treatment step complicated, has a high possibility of mixing of impurities and sometimes damages the inherent functions of the cells due to the denaturation or the damage of proliferated cells by the chemical treatment.

In order to overcome these defects, several techniques have been proposed. Of them, particularly Japanese Patent Application No. 2001-226141 (Japanese Laid-open Patent Publication No. JP 2003-38170A) has enabled the preparation of a cell sheet having sufficient strength by culturing an anterior eye part-related cell on a cell culture support composed of a base material whose surface is coated with a temperature-responsive polymer having an upper limit or lower limit critical dissolution temperature in water of 0 to 80° C., if necessary or required, making the cultured cell layer a multilayer by the conventional method and detaching the cultured cell sheet only by changing the temperature of the support. Further, this cell sheet maintains a basement ligament-like protein as well and clearly improves bioadherence to tissues compared to the above described dispase-treated cell sheet. Further, according to WO/2002/008387, by culturing cells of the heart muscle tissue on a cell culture support comprising a base material coated with a temperature-responsive polymer to obtain a heart muscle-like cell sheet, thereafter changing the culture fluid temperature to the upper limit critical dissolution temperature or higher or to the lower limit critical dissolution temperature or lower, allowing the multilayered cultured cell sheet to adhere to a polymer film and detaching the cell sheet together with the polymer film, and further making the cell sheet a three-dimensional structure, it was found that a cell sheet having several functions with a reduced structural defect as a heart muscle-like tissue in vitro and a three-dimensional structure could be constructed. However, in both methods, no examination on the regeneration of the periodontal ligament and the acquirement of connective tissue adherence has been made.

DISCLOSURE OF THE INVENTION

Problems to be Solved by the Invention

The present invention is made to intend to solve the above described conventional technical problems. Specifically, the present invention has an object to provide a highly bioadherent cultured periodontal ligament cell sheet having good adherence to the dental root surface. Further, the present invention has an object to provide a process for producing the same and a method of use thereof.

Means to Solve the Problems

In order to solve the above described problems, investigations have been made from various aspects by the present inventors to perform research and development. As a result, it is found that a highly bioadherent cultured periodontal ligament cell sheet having extremely high adherence to the dental root surface can be obtained by culturing, under specified conditions, periodontal ligament cells on a cell culture support composed of a base material whose surface is covered with a temperature-responsive polymer, thereafter regulating the temperature of the culture fluid to the upper limit critical dissolution temperature or higher or to the lower limit critical dissolution temperature or lower, allowing the cultured periodontal ligament cell sheet resulting from the culturing to adhere to a specified carrier and detaching the cell sheet together with the carrier while suppressing the shrinkage of the cell sheet. The present invention has been completed based on such knowledge.

In other words, the present invention provides a highly bioadherent cultured periodontal ligament cell sheet which extremely well adheres to the dental root surface and is allowed to adhere to a carrier.

Further, the present invention provides a process for producing a highly bioadherent cultured periodontal ligament cell sheet comprising culturing cells on a cell culture support composed of a base material whose surface is covered with a temperature-responsive polymer having an upper limit or lower limit critical dissolution temperature in water of 0 to 80° C. under specified conditions, thereafter (1) regulating the temperature of the culture fluid to the upper limit critical dissolution temperature or higher or to the lower limit critical dissolution temperature or lower, (2) allowing the cultured periodontal ligament cell sheet resulting from the culturing to adhere to a carrier and (3) detaching the sheet intact together with the carrier.

In addition, the present invention provides the above described highly bioadherent cultured periodontal ligament cell sheet for partially or entirely treating a damage or defect of the affected part in periodontal tissues.

Furthermore, the present invention provides a treatment method comprising transplanting the above described highly bioadherent cultured periodontal ligament cell sheet into a partial or the entire damage or defect of the affected part in periodontal tissues.

Advantageous Effect of the Invention

The highly bioadherent regenerated periodontal ligament cell sheet obtained in the present invention has extremely high bioadherence to the dental root surface and, for example, according to the GTR method, the cell migration from the peripheral tissues (mainly the residual periodontal ligament) has been merely passively expected but the use of the cell sheet of this invention enables transplantation of target cells at a very high density. Further, although the intrusion of the epithelial cell in the healing process is a big problem, early occurrence of immobilization of the cells to the dental root surface could prevent it. The cell sheet of the present invention is quickly immobilized to the dental root surface to advantageously act on the inhibition of intrusion of the epithelial cell. Furthermore, lamination of cell sheets to be transplanted can be endowed with a tree-dimensional polarity to more efficiently reconstruct an adhesion apparatus and its clinical application to moderate periodontitis, sever periodontitis, gingival recession and the like is highly promising. Accordingly, the present invention is a very useful invention in the field of medicine, biology and the like including, for example, cellular engineering and medical engineering and the like.

BEST MODE FOR CARRYING OUT THE INVENTION

Figure 1:
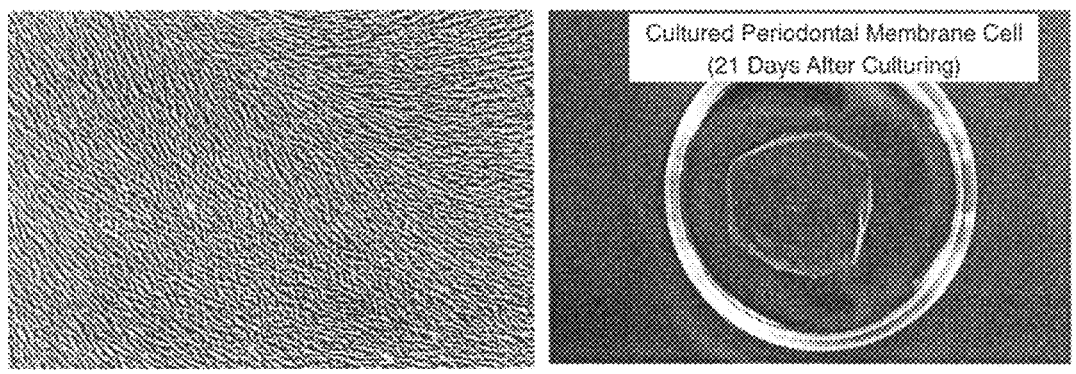
FIG. 1 shows the state of the cells 21 days after culturing shown in Example 2 (left Figure) and the state of the cells detached without using a carrier (right Figure).

The present invention provides a cultured periodontal ligament cell sheet having a syndesmotic microstructure ("syndesmostic" indicates the state of a cultured periodontal ligament cell sheet which adheres to the dentin and is oriented) adhering to a carrier. The cells which are suitably used in the preparation of the cultured periodontal ligament cell sheet of this invention include periodontal fibroblasts and a mixture of periodontal fibroblasts and at least one type of cementoblasts, osteoblasts, gingival fibroblasts, endothelial cells and mesenchymal stem cells, and their types are not limited. In the present invention, the highly bioadherent regenerative periodontal ligament cell sheet means a sheet obtained by culturing the above described cells on a culture support in the form of a single layer and thereafter detaching the resulting cell sheet from the support. The obtained cell sheet has a lower side surface in contact with the culture support on culturing and an upper side surface opposite thereto. By utilizing a cell culture support composed of a base material whose surface is covered with a temperature-responsive polymer having an upper limit or lower limit critical dissolution temperature in water of 0 to 80° C. according to this invention in culturing the cells, adhesion proteins produced by the cells by themselves on culturing are abundantly present on the lower side surface of the cell sheet.

The highly bioadherent cultured periodontal ligament cell sheet of this invention may be a single layer sheet of the above described periodontal ligament fibroblasts or a mixture of the periodontal ligament fibroblasts and at least one type of cementoblasts, osteoblasts, gingival fibroblasts, endothelial cells and mesenchymal stem cells or a laminated sheet of the single layer sheets. Here, the laminated sheet may be a laminated sheet of the highly bioadherent cultured periodontal ligament cell sheets alone or a laminated sheet of a combination of the highly bioadherent cultured periodontal ligament cell sheet with a sheet composed of another type of cells and includes, for example, a laminated cell sheet obtained by laying a cell sheet of the above described periodontal ligament fibroblasts or a mixture of the periodontal ligament fibroblasts and at least one type of cementoblasts, osteoblasts, gingival fibroblasts, endothelial cells and mesenchymal stem cells on a cell sheet of the periodontal ligament fibroblasts and a laminated cell sheet obtained by laying a cultured cell sheet composed of at least one type of cementoblasts, osteoblasts, gingival fibroblasts epithelial cells and mesenchymal stem cells on the above described single layer sheet, and the laminated cell sheet is not particularly limited. Further, the position and the order of lamination and the number of lamination are not particularly limited. For example, a laminated cell sheet obtained by laying a single layer cell sheet of the above described periodontal ligament fibroblasts or a mixture of the periodontal ligament fibroblasts and at least one type of cementoblasts, osteoblasts, gingival fibroblasts, endothelial cells and mesenchymal stem cells on one or both of the upper side and the lower side of the same single layer cell sheet, a laminated cell sheet obtained by laying a cell sheet composed of at least one type of cementoblasts, osteoblasts, gingival fibroblasts, endothelial cells and mesenchymal stem cells on one or both of the upper side and the lower side of the above described single layer cell sheet and a laminated cell sheet obtained by laying a cell sheet of a mixture of periodontal ligament fibroblasts and at least one type of cementoblasts, osteoblasts, gingival fibroblasts, endothelial cells and mesenchymal stem cells on a single layer cell sheet of the periodontal ligament fibroblasts or a mixture of the periodontal ligament fibroblasts and at least one different type of cementoblasts, osteoblasts, gingival fibroblasts, endothelial cells and mesenchymal stem cells may be suitably used. Furthermore, the laminated cell sheet obtained by laying a cell sheet composed of osteoblasts on the upper side of a single layer cell sheet composed of the periodontal ligament fibroblasts or a mixture of the periodontal ligament fibroblasts and at least one type of cementoblasts, osteoblasts, gingival fibroblasts, endothelial cells and mesenchymal stem cells and furthermore laying a cell sheet composed of cementoblasts on the lower side of the cell sheet composed of the periodontal ligament fibroblasts and the laminated sheet obtained by laying a cell sheet composed of gingival fibroblasts on the upper side of a single layer cell sheet composed of the periodontal ligament fibroblasts or a mixture of periodontal ligament fibroblasts and at least on type of cementoblasts, osteoblasts, gingival fibroblasts, endothelial cells and mesenchymal stem cells, further laying a cell sheet composed of osteoblasts on the cell sheet of the gingival fibroblasts and still further laying a cell sheet composed of cementoblasts on the lower side of the cell sheet composed of the periodontal ligament fibroblasts or a mixture of the periodontal ligament fibroblasts and at least on type of cementoblasts, osteoblasts, gingival fibroblasts, endothelial cells and mesenchymal stem cells may be suitably. The number of lamination may be at most eight and is preferably at most six, more preferably at most four. The number of lamination of eight or more does not allow oxygen and nutrients to reach the central part of the cell sheet to result in the death of cells, and thus is not preferred.

The culture medium composition for culturing the above described cells in the present invention is not particularly limited, and the medium composition conventionally used in culturing these types of cells may be used. For example, as the culture medium on culturing a cell sheet of periodontal ligament fibroblasts or a mixture of periodontal ligament fibroblasts and at least one type of cementoblasts, osteoblasts, gingival fibroblasts, endothelial cells and mesenchymal stem cells, the α-MEM medium, the DMEM medium or their mixture supplemented with 10% bovine serum or the mixture further supplemented with ascorbic acid diphosphate ester at a concentration of 50 μg/ml may be suitably used.

The highly bioadherent cultured periodontal ligament cell sheet in this invention does not undergo damage by a protease represented by dispase, trypsin and the like. Accordingly, the highly bioadherent cultured periodontal ligament cell sheet detached from the base material maintains a cell-cell desmosome structure and has a reduced structural defect and high strength. The sheet of this invention does not undergo the destruction of a basement ligament-like protein between the cell and the base material. As a result of this, the cell sheet can well adhere to the tissue of the affected part and an efficient treatment can be performed. Specifically explaining the above, when the conventional protease such as dispase and trypsin is used, the cell-cell desmosome structure, the basement ligament-like protein between the cell and the base material and the like can hardly be maintained and accordingly, the cells are detached in an individually separated state. Of them, as to the dispase of a protease, it is known that the cell-cell desmosome structure can be detached while maintaining 10 to 60% of the desmosome structure but the basement ligament-like protein between the cell and the base material and the like are mostly destructed and thus, the strength of the obtained cell sheet is low. Contrast to this, the cell sheet of this invention is in the state of maintaining 80% or more of both the desmosome structure and the basement ligament-like protein and can obtain the above described various effects.

The highly bioadherent cultured periodontal ligament cell sheet in this invention extremely well bioadheres to the dental root surface of living tissues. This property is found by the realization of suppressing the shrinkage of a cultured periodontal ligament cell detached from the support surface. In this instance, the shrinkage factor of the cultured periodontal ligament cell sheet is desirably 20% or less in any direction within the sheet, preferably 10% or less, more preferably 5% or less. With the shrinkage factor in length in any direction of the sheet of 20% of more, the detached cell sheet slackens and does not adhere to tissues in the slack state even by allowing the cell sheet to adhere to living tissues, and the bioadherence which this invention exhibits cannot be expected.

The method of causing no shrinkage of the cultured periodontal ligament cell sheet is not limited if the method does not shrink the cell sheet and includes, for example, a method of allowing the cell sheet to adhere to a carrier whose central part is cut in the form of a ring and detaching the cell sheet together with the carrier.

The carrier used in allowing the cultured periodontal ligament cell sheet to adhere is a structure for holding the cell sheet not to shrink and, for example, a polymer ligament, a structure molded from a polymer ligament, a metallic jig and the like can be used. For example, when a polymer is used as the material for the carrier, its specific material includes, for example, polyvinylidene difluoride (PVDF), polypropylene, polyethylene, cellulose, its derivative, paper, chitosan, chitin, collagen and urethane.

The adherence in this invention means the state where on the boundary surface between the cell sheet and the carrier, the cell sheet neither slides nor moves on the carrier so as for the cell sheet not to shrink, and the cell sheet may adhere to the carrier by physical bonding or through a fluid (for example, a culture fluid and other isotonic solutions) present in between the both.

The shape of the carrier is not particularly limited and in transplanting the obtained highly bioadhesive cultured periodontal ligament cell sheet, the use of a carrier part of which is cut to the same size as the size of the site to be transplanted or a size larger than the size of the site to be transplanted immobilizes the cell sheet only on the peripheral part of the cut carrier, and the cell sheet present on the cut part of the carrier may only be advantageously applied to the site to be transplanted.

Further, high bioadherence to the dental root surface which is a characteristic feature of the cultured periodontal ligament cell sheet in this invention can be realized under specified culturing conditions. In other words, the cultured periodontal ligament cell sheet of this invention can be obtained by seeding periodontal ligament cells on the support surface and thereafter culturing the cells and is found suitable typically at most 21 days after the cells become confluent (in a completely full state), preferably at most 15 days and more preferably at most 10 day. More than 21 days after the cells become confluent, the activity of the cells in the lowermost layer of the detached cell sheet is reduced resulting in the reduction of adherence and, as the result, high bioadherence which this invention exhibits cannot be expected.

The dental root surface of this invention is not particularly limited if it is any dental root part and generally includes, for example, part or the entire of a damage or defect in the affected part in periodontal tissues. The method of utilizing the high bioadherent cultured periodontal ligament cell sheet of this invention for this dental root surface is not particularly limited and includes, for example, a method of covering the dental root surface with the high bioadherent cultured periodontal ligament cell sheet of this invention. In this instance, the cultured periodontal ligament cell sheet may be suitably cut along the size and the shape of the affected part. Thus, the high bioadherent cultured periodontal ligament cell sheet of this invention can extremely well adhere to the living tissue of the dental root surface and could not be obtained from the prior art.

The temperature-responsive polymer which is used in coating the base material of a cell culture support has an upper limit critical dissolution temperature or a lower limit critical temperature in an aqueous solution of 0° C. to 80° C., preferably 20° C. to 50° C. Upper limit critical dissolution temperatures or lower limit critical temperatures of higher than 80° C. may perish the cells and are not preferred. Further, upper limit critical dissolution temperatures or lower limit critical temperatures of lower than 0° C. generally extremely reduce the rate of proliferation of the cells or perish the cells and are not preferred either.

The temperature-responsive polymer which is used in this invention may be either a homopolymer or a copolymer. Such polymers include, for example, the polymers described in Japanese Laid-open Patent Publication A No. 02-211865. Specifically, the temperature-responsive polymer can be obtained by homopolymerization or copolymerization of the monomers shown below. The usable monomers include, for example, (meth)acrylamide compounds, N-(or N,N-di)alkyl substituted (meth)acrylamide derivatives and vinyl ether derivatives. In the case of copolymers, any two or more monomers out of these compounds can be used. Furthermore, copolymers with monomers other than the above described monomers, graft copolymers of polymers with each other or a mixture of a polymer and a copolymer may be used. It is also possible to crosslink within the range of not adversely affecting the inherent properties of the polymer.

The base material to be coated include glass, modified glass, a compound such as polystyrene and polymethyl methacrylate, and substances capable of generally imparting a form, for example, polymer compounds other than the above described ones and ceramics may all be used.

The method of coating the temperature-responsive polymer on the support is not particularly limited and may follow the method described Japanese Laid-open Patent Publication A No. 02-211865. Specifically, this coating can be performed by any one of electron beam irradiation (EB), γ-ray irradiation, ultraviolet ray irradiation, plasma treatment, corona treatment and organic polymerization reaction of the above described monomer or polymer together with the base material, and further by physical adsorption such as coating and kneading.

The amount of the temperature-responsive polymer coated may be in the range of 0.5 to 5.0 $\mu g/cm^2$, preferably 1.0 to 4.0 $\mu g/cm^2$ and more preferably 1.2 to 3.3 $\mu g/cm^2$. Amounts of less than 0.5 $\mu g/cm^2$ are hard to detach the cells on the above described polymer even when stimulation is applied to remarkably worsen working efficiency, and thus are not suitable. On the other hand, with amounts of more than 5.0 $\mu g/cm^2$, the adhesion of the cells is hard in its region to render sufficient adhesion of cells difficult. The shape of the support in this invention is not particularly limited and includes, for example, a dish, a multiplate, a flask, and a cell insert.

In this invention, the culture of cells is performed on the cell culture support prepared in the above described manner. When the above described polymer coated on the support surface has a upper limit critical dissolution temperature, the culture medium temperature is not particularly limited if is not higher than the upper critical dissolution temperature and in the case of the polymer having a lower limit critical dissolution temperature, the culture medium temperature is not particularly limited if it is not lower than the lower limit critical dissolution temperature. However, the cell culture in a low temperature region where the culture cells do not proliferate or in a high temperature region where the culture cells perish is naturally inappropriate. The culture conditions other than temperature may follow the conventional method and are not particularly limited. For example, as the culture medium to be used, a medium added with the conventional serum such as fetal calf serum (FCS) may be used and a nonserum culture medium free of such serum may also be used.

In order to detach and recover cultured cells from the support material in the method of this invention, by allowing the cultured highly bioadherent cultured periodontal ligament cell sheet to adhere to a carrier and raising the temperature of the cell-adhering support material to the upper limit critical dissolution temperature of the polymer coated on the support base material or higher or lowering the temperature of the cell-adhering support material to the lower limit critical dissolution temperature of the polymer or lower, the highly bioadherent cultured periodontal ligament cell sheet can be detached together with the carrier. Further, the sheet can be detached in the culture fluid where the cells have been cultured and also can be detached in other isotonic fluids, and thus the method of detaching the sheet can be selected in accordance with the object.

In the present invention, the cell sheet is applied to the affected part and thereafter the carrier may be removed from the cell sheet. This method of removing the cell sheet is not particularly limited and, for example, a method of removing the cell sheet by moisturizing the carrier and weakening the adhesion of the carrier to the cell sheet or a method of removing the cell sheet by cutting with the use of a jig such as a scalpel, scissors, a laser beam and a plasma wave may be used. For example, in the case of using the cell sheet adhering to the carrier part of which has been cut as described above, when the cell sheet is cut along the borderline of the affected part with the use of a laser beam or the like, adherence of the cell sheet to the part other than the affected part can be advantageously avoided.

The method of immobilizing the highly bioadherent cultured periodontal ligament cell sheet which this invention shows to living tissues is not particularly limited, and bonding of the cell sheet to the living tissues with an adhesive usable in the living body or stitching of the cell sheet and the living tissues may be effective or since the highly bioadherent cultured periodontal ligament cell sheet which this invention shows quickly adheres to the living body tissues, the cell sheet may only be applied to the affected part without using these means.

The laminated sheet in this invention is not particularly limited in its lamination method, and the above described highly bioadherent cultured periodontal ligament cell sheet adhering to the carrier may be laminated in the following methods.

(1) A method of making a multilayered cell sheet by repeating the steps of allowing a cell sheet adhering to a carrier to adhere to a cell culture support, thereafter adding a culture medium to remove the carrier from the cell sheet and further allowing another cell sheet adhering to a carrier to adhere to the cell sheet.
(2) A method of making a multilayered cell sheet by repeating the steps of immobilizing a cell sheet adhering to a carrier on a reversed cell culture support at the carrier side, allowing another cell sheet to adhere to the cell sheet side, thereafter adding a culture medium to remove the carrier from the cell sheet, and again allowing another cell sheet to adhere to the cell sheet.
(3) A method of allowing the cell sheets each adhering to a carrier to adhere to each other at the cell sheet side.
(4) A method of applying the cell sheet adhering to a carrier to the affected part of a living body to allow the cell sheet to adhere to the living tissues, thereafter removing the carrier and again layering another cell sheet on the cell sheet adhering to the living body tissues.

In order to detach and recover the highly bioadherent cultured periodontal ligament cell sheet in high yield, the method of softly striking or shaking the cell culture support and a method of stirring the culture medium with a pipette and the like may be used singly or as a combination. Additionally, if necessary or required, the cultured cells may be washed with an isotonic fluid or the like and thereafter is detached and recover.

The use of the highly bioadherent cultured periodontal ligament cell sheet shown in this invention is not particularly limited and is effective, for example, for moderate periodontitis, severe periodontitis and other periodontium-related diseases and gingiva-related diseases such as gingival recession and gingivitis.

The highly bioadherent cultured periodontal ligament cell sheet obtained in the above described methods is very superior in non-invasion on removal of the cell sheet to the cell sheet obtained by the conventional method and is highly promising as a periodontal ligament for transplantation or the like in clinical application. Particularly, the highly bioadherent cultured periodontal ligament cell sheet of this invention has high bioadherence to living tissues differently of the conventional transplant sheet, and accordingly quickly adheres to the living tissues. Although only passive cell migration from periodontal tissues (mainly the residual periodontal ligament) is expected in GTR, the use of this cell sheet enables transplantation of target cells at a very high density due to this property of the cell sheet. Further, due to the use of own cells, the problem of antigenicity/infection can be solved. Viewed from cell transplantation, the study of transplanting the cells which are three-dimensionally cultured in a collagen gel together with the gel, the study of seeding cells on a bioabsorptive ligament and transplanting the cultured cell together with the ligament and the like are advanced but as to the cell density, it is clear that the cell sheet is overwhelmingly superior and the cell sheet having a pure cellular/extracellular substrate component alone which is free of an intervening material such as the absorptive ligament is advantageous in immobilizing the cell sheet on tissues. Invasion of the epithelium in the healing process is a big problem but this problem can be prevented if the connective tissue cells have previously been immobilized on the dental root surface. In this immobilization of cells on the dental root surface, the extracellular substrate containing adhesion molecules secreted from the cultured cells and the cells are simultaneously non-invasively recovered and transplanted, and accordingly is expected to advantageously act on early immobilization of the transplanted cells to the dental root surface. The adhesion apparatus present in the periphery of teeth has a special stratum structure of cementum, periodontal ligament (ligament part) and alveolar bone. It is confirmed from the studies made heretofore that the cells capable of reconstructing periodontal ligament tissues exist neither in the alveolar bone nor in the gingiva but only in the periodontal ligament in the periodontal tissue. Further, in the periodontal ligament, various types of cells exist (osteoblasts constituting the support alveolar bone, fibroblasts constituting the ligament of the periodontal ligament, cementoblasts constituting the cementum and unconfirmed stem cells being naturally thought to exist) and the study of separating these cells is advanced, and by separating cells from the periodontal ligament to prepare a cell sheet and laminating the cell sheets on transplantation to allow the cell sheet to possess a three-dimensional polarity, an adhesion apparatus can be thought to be more efficiently reconstructed. The above can be thought to be a very effective technique for improving the healing efficiency of the affected part and furthermore alleviating the load of a patient.

EXAMPLE

The present invention will now be explained in more detail based on examples but these examples are not to limit the present invention.

Examples 1 and 2

Figure 2:
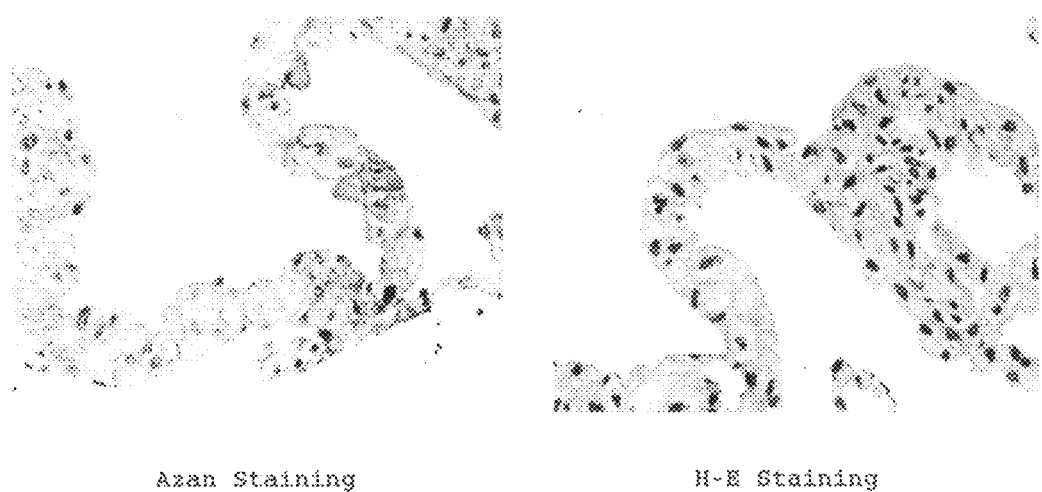
FIG. 2 is photographs showing the results of azan staining and hematoxylin and eosin (H-E) staining of a cultured periodontal ligament cell sheet shown in Example 2.
Figure 3:
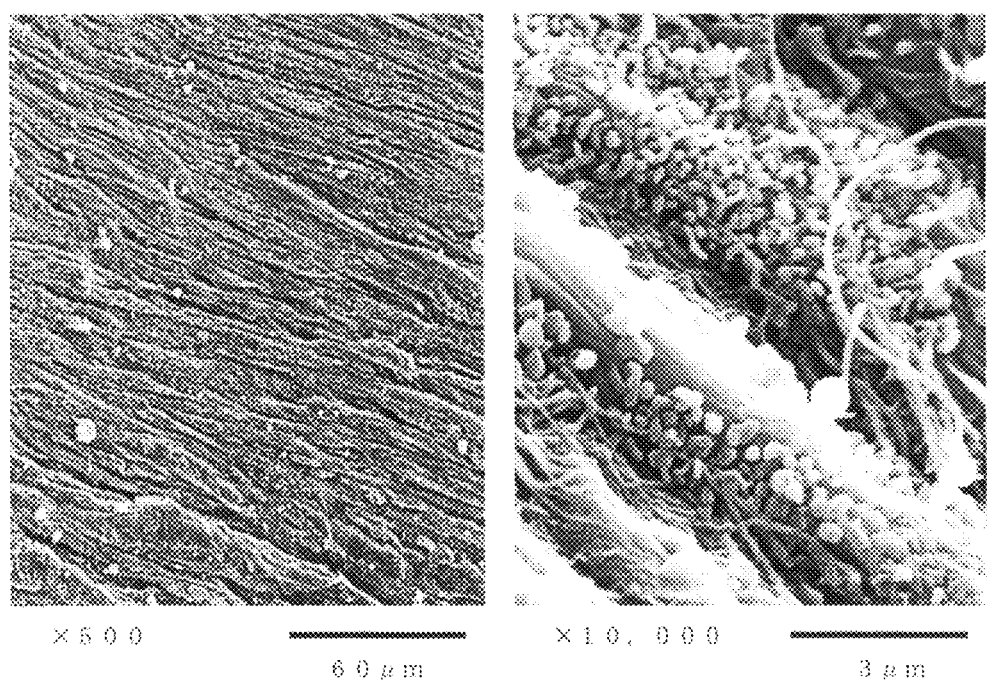
FIG. 3 are scanning electronic microscopic photographs having a magnification of ×500 (left Figure) and ×10,000 (right Figure) showing the results of observing the surface of a cultured periodontal ligament cell sheet shown in Example 2.
Figure 4:
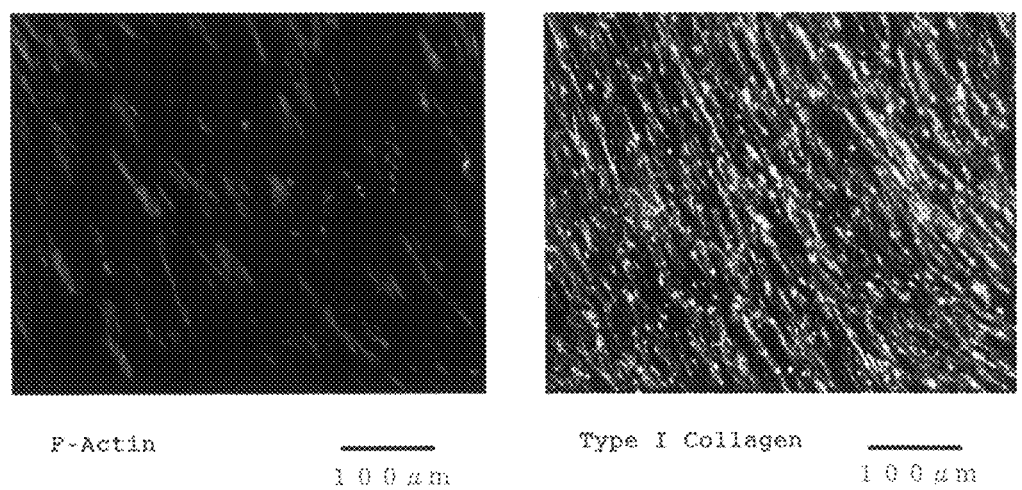
FIG. 4 shows diagrams of the results of staining F-actin and I type collagen on the surface of a cultured periodontal ligament cell sheet shown in Example 2 by the conventional method.

On commercially available 3.5 cmϕ culture dishes (FALCON 3001, a product of Becton Dickinson Labware), 0.07 ml of a 53% solution of an N-isopropyl acrylamide monomer dissolved in isopropyl alcohol (Example 1) and 0.07 ml of a 54% solution of the N-isopropyl acrylamide dissolved in isopropyl alcohol (Example 2) were coated, respectively. The obtained culture dishes were irradiated with an electron beam having an intensity of 0.25 MGy to immobilize an N-isopropyl acrylamide polymer (PIPAAm) on the culture dish surfaces. After the irradiation, the culture dishes were washed with ion-exchanged water to remove the remaining monomer and the PIPAAm unattached to the dishes, dried in a clean bench, and sterilized with an ethylene oxide gas to obtain cell culture support materials. When the amount of the temperature-responsive polymer on the substrate surface was measured, it was found that 1.8 μg/cm$^2$ (Example 1) and 2.0 μg/cm$^2$ (Example 2) were coated, respectively. Periodontal ligament tissues were collected from the maxillary molar part of an F344 nude rat and subjected to enzyme treatment according to the conventional method to recover periodontal ligament cells which were then seeded (1×10$^5$ cells/3.5 cm dish) on respective carrier material surfaces. As a medium, the DMEM medium supplemented with 10% bovine serum and 50 μg/ml ascorbic acid diphosphate ester was used. As the result of culturing at 37° C. under 5% CO$_2$, the periodontal ligament cells normally adhered to both cell culture carrier materials and proliferated. After 14 days, the cultured cells became confluent, and further culturing was continued for 7 days, and thereafter a 2 mmϕ disk carrier molded by cutting a 5 mmϕ polyvinylidene difluoride (PVDF) ligament was covered on the cells thus cultured and by quietly sucking the medium, incubating the cells together with each of the cell culture support materials at 20° C. for 30 minutes and cooling, the cells on both cell culture support materials were detached together with the covered carrier. The obtained cell sheets had sufficient strength as one sheet having a shrinkage factor of 5% or less. Further, in each of the above described examples, the "low temperature treatment" was carried out under the conditions of incubation at 20° C. for 30 minutes but the "low temperature treatment" in the present invention is not limited to these temperature and time. A preferred temperature condition as the "low temperature treatment" in the present invention is 0° C. to 30° C. and a preferred treatment time is two minutes to one hour. The state of the cells 21 days after the culturing in Example 2 is shown in FIG. 1, left Figure and the state on detaching without using a carrier is shown in FIG. 1, right Figure. The results of subjecting the cultured periodontal ligament cell sheet obtained in Example 2 to azan staining and the H-E staining according to the conventional method are shown in FIG. 2. Further, the results of observing the surface of the periodontal ligament sheet obtained in Example 2 by a scanning electron microscopic photographs at a magnification of ×500 (left Figure) and ×10,000 (right Figure) are shown. It would be understood that the structure specific to the periodontal ligament on the cell sheet surface did not suffer damage. Furthermore, FIG. 4 shows the result of staining F-actin and type I collagen on the surface of the cultured periodontal ligament sheet obtained in Example 2 according to the conventional method. It would be understood that both proteins remain and the cultured periodontal ligament cell sheet obtained in the present invention has reduced damage.

Example 3

Figure 5:
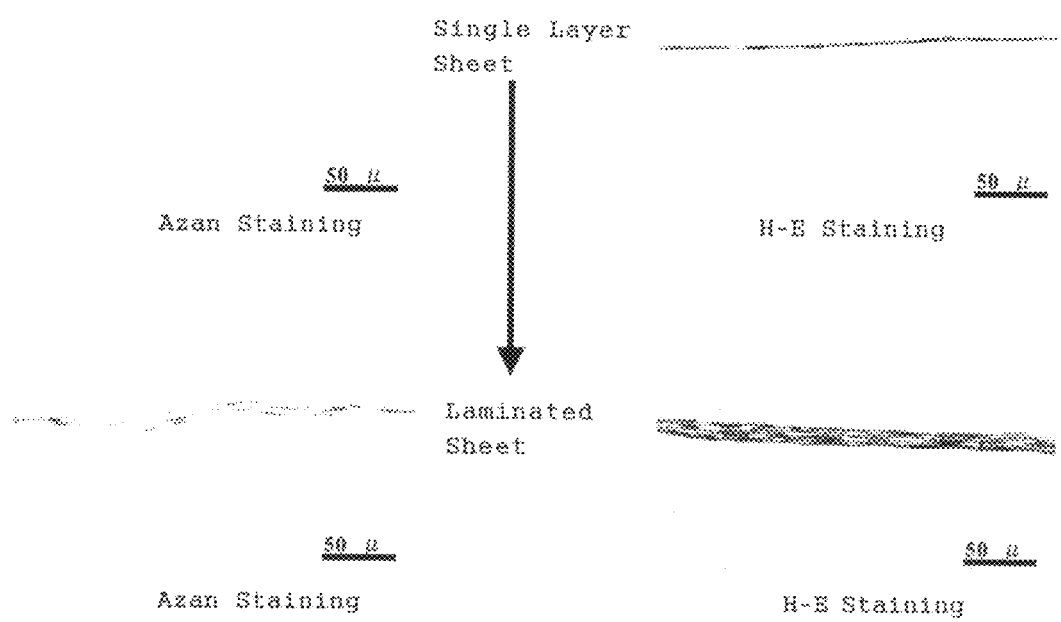
FIG. 5 shows a diagram showing the results of comparative examination of the azan staining and the H-E staining of a cultured periodontal ligament cell sheet (in the form of a single layer) shown in Example 2 and a three-layered laminated cell sheet shown in Example 3.

A cell culture support material was obtained in the same manner as in Example 2 except that 0.07 ml of a 50% solution of an N-isopropyl acrylamide dissolved in isopropyl alcohol was coated on the above described commercially available 3.5 cmϕ culture dish (FALCON 3001). When the amount of the temperature-responsive polymer on the substrate surface was measured, it was found that 2.1 μg/cm$^2$ was coated. Periodontal ligament tissues were collected from the maxillary molar part of an F344 nude rat and subjected to enzyme treatment according to the conventional method to recover cementoblasts and osteoblasts. Each type of the cells was separately seeded (1×10$^5$ cells/3.5 cm dish) on the support material surface. As a medium, the DMEM medium supplemented with 10% bovine serum and 50 μg/ml ascorbic acid diphosphate ester was used. As the result of the culturing at 37° C. under 5% CO$_2$, each type of the cells on the culture support material normally adhered and proliferated. Each type of the cells became confluent 14 days after culturing. Culturing was further continued for 7 days, and thereafter the cultured periodontal ligament cell sheet recovered in Example 2 was first laminated on the cementoblast sheet while adhering to the support material. Thereafter, the carrier adhering to the cultured periodontal ligament cell sheet was removed to obtain a laminated sheet of the cementoblast sheet and the cultured periodontal ligament cell sheet. In this instance, this laminated sheet was maintained while adhering to the support material surface. Next, the confluent osteoblast sheet was detached. The process was carried out in the same manner as in Example 2. The obtained osteoblast sheet had a shrinkage factor of 3% or less and sufficient strength as one sheet. This osteoblast sheet was laminated on the sheet obtained by laying the cultured periodontal ligament cell sheet on the cementoblast sheet, and these sheets were allowed to adhere to one another to obtain a three-layered laminated sheet of the cementoblast sheet, the cultured periodontal ligament sheet and the osteoblast sheet in the order named from the surface of the culture support material. Finally, by cooling the cell culture support to which the cementoblast sheet adhered, the three-layered laminated cell sheet was detached. The results of subjecting the (single layer) cultured periodontal ligament cell sheet obtained in Example 2 and the three-layered laminated cell sheet obtained in Example 3 to azan staining and H-E staining according to the conventional method are shown in FIG. 5. It would be understood that the ligament thickness is increased by lamination.

Example 4

Figure 6:
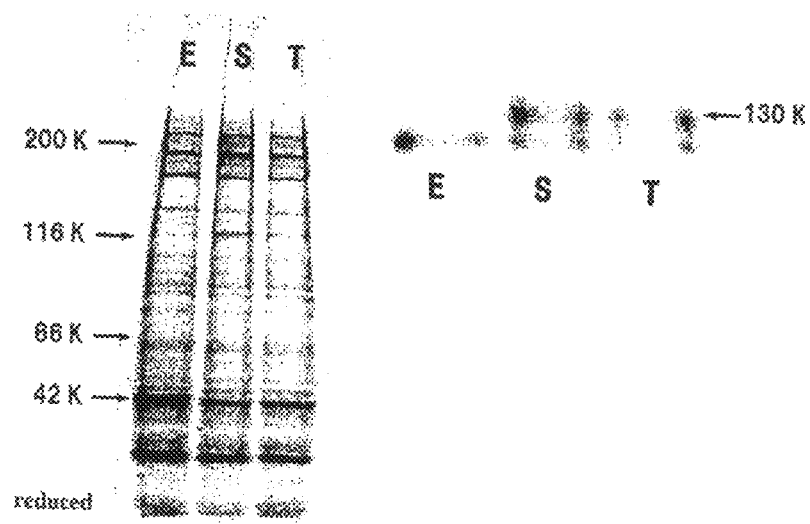
FIG. 6 shows the results of examining integrin β1 remaining in the cultured periodontal ligament cells shown in Example 4, Comparative Examples 1 and 2.
Figure 7:
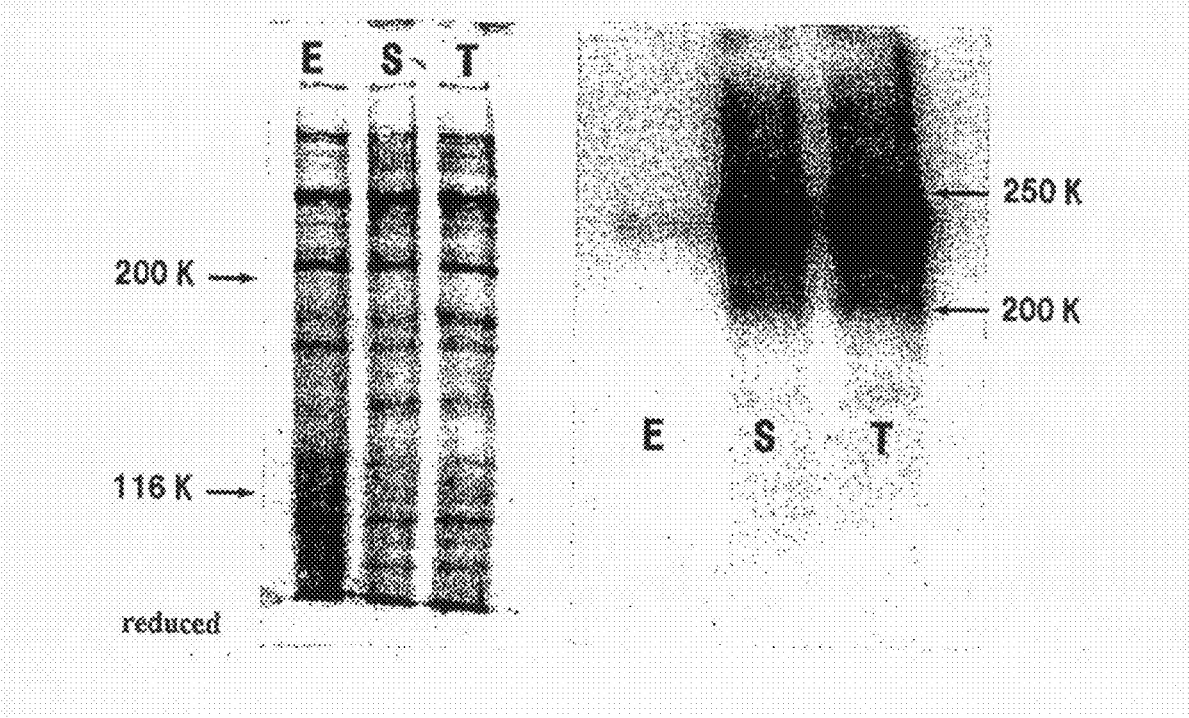
FIG. 7 shows the results of examining fibronectin remaining in the cultured periodontal ligament cells shown in Example 4, Comparative Examples 1 and 2.

Integrin β1 and fibronectin which are known as adhesion proteins present in the cultured periodontal ligament cell sheet obtained in Example 2 were confirmed by the immunoblotting technique according to the conventional method. The obtained results are shown in FIG. 6 (T in the Figure) and FIG. 7 (T in the Figure), respectively. Both adhesion proteins also remain at a high concentration and high bioadherence of the cell sheet of this invention can be expected.

Comparative Example 1

On the above described commercially available 3.5 cmϕ culture dish (FALCON 3001, uncoated with a temperature-responsive polymer), periodontal ligament cells were cultured in the same manner as in Example 2. Twenty-one days after culturing, the cultured periodontal ligament cells were recovered by performing the trypsin-EDTA treatment according the conventional method. The obtained results are shown in FIG. 6 (E in the Figure) and FIG. 7 (E in the Figure), respectively. Both adhesion proteins remained only at a low concentration, and thus the cultured periodontal ligament cells were not suitable as the cell sheet of this invention.

Comparative Example 2

On the above described commercially available 3.5 cmϕ culture dish (FALCON 3001, uncoated with a temperature-responsive polymer), periodontal ligament cells were cultured in the same manner as in Example 2. Twenty-one days after culturing, the cultured periodontal ligament cells were mechanically detached and recovered with the use of a rubber blade. The results ware shown in FIG. 6 (S in the Figure) and FIG. 7 (S in the Figure), respectively. Both adhesion proteins remained at a high concentration but the cell sheet underwent mechanical action to be cut, and thus was not suitable as the cell sheet of this invention.

Example 5

Figure 8:
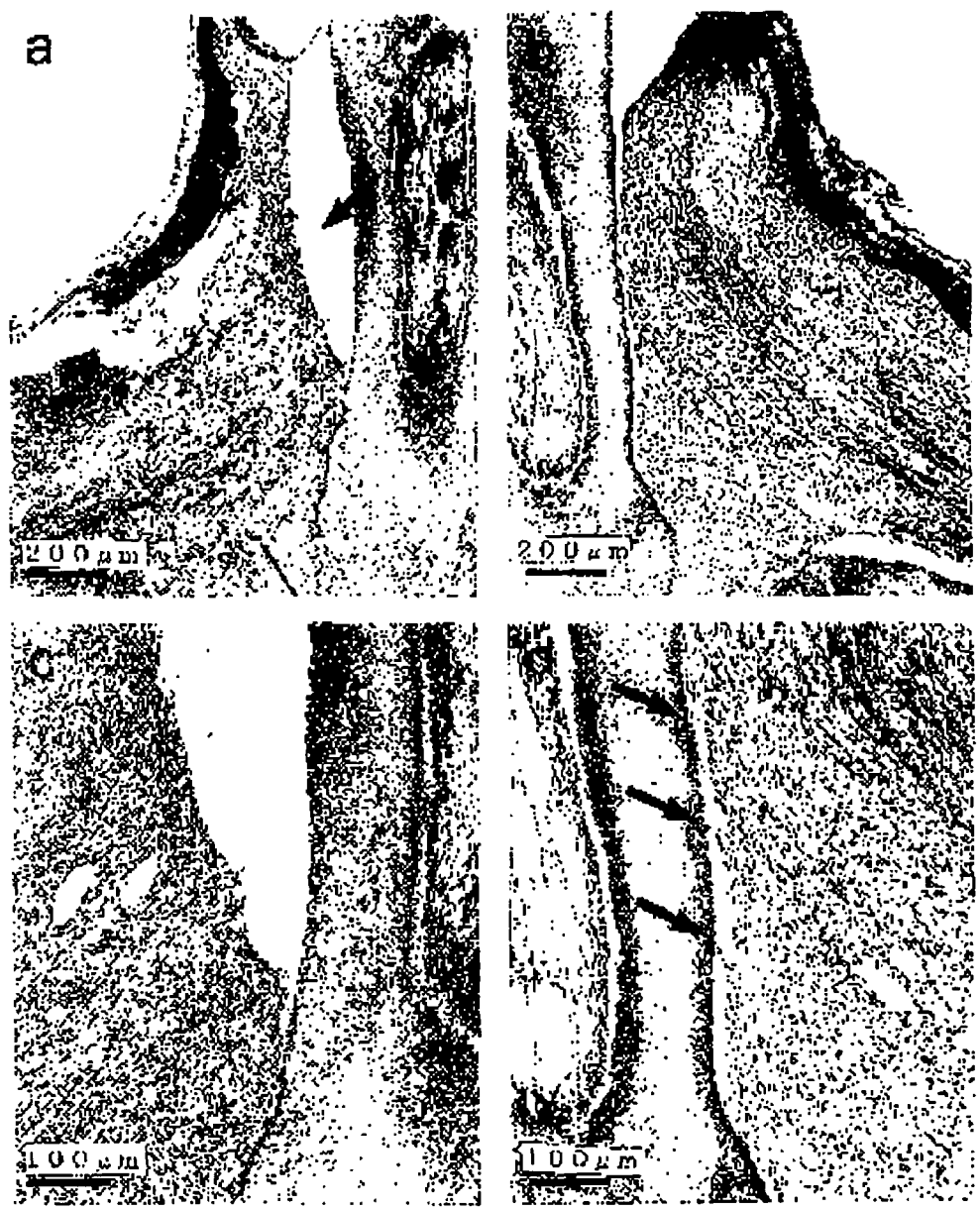
FIG. 8 shows the healing state of periodontal tissues one week after the operation shown in Example 5 and Comparative Example 3.
Figure 9:
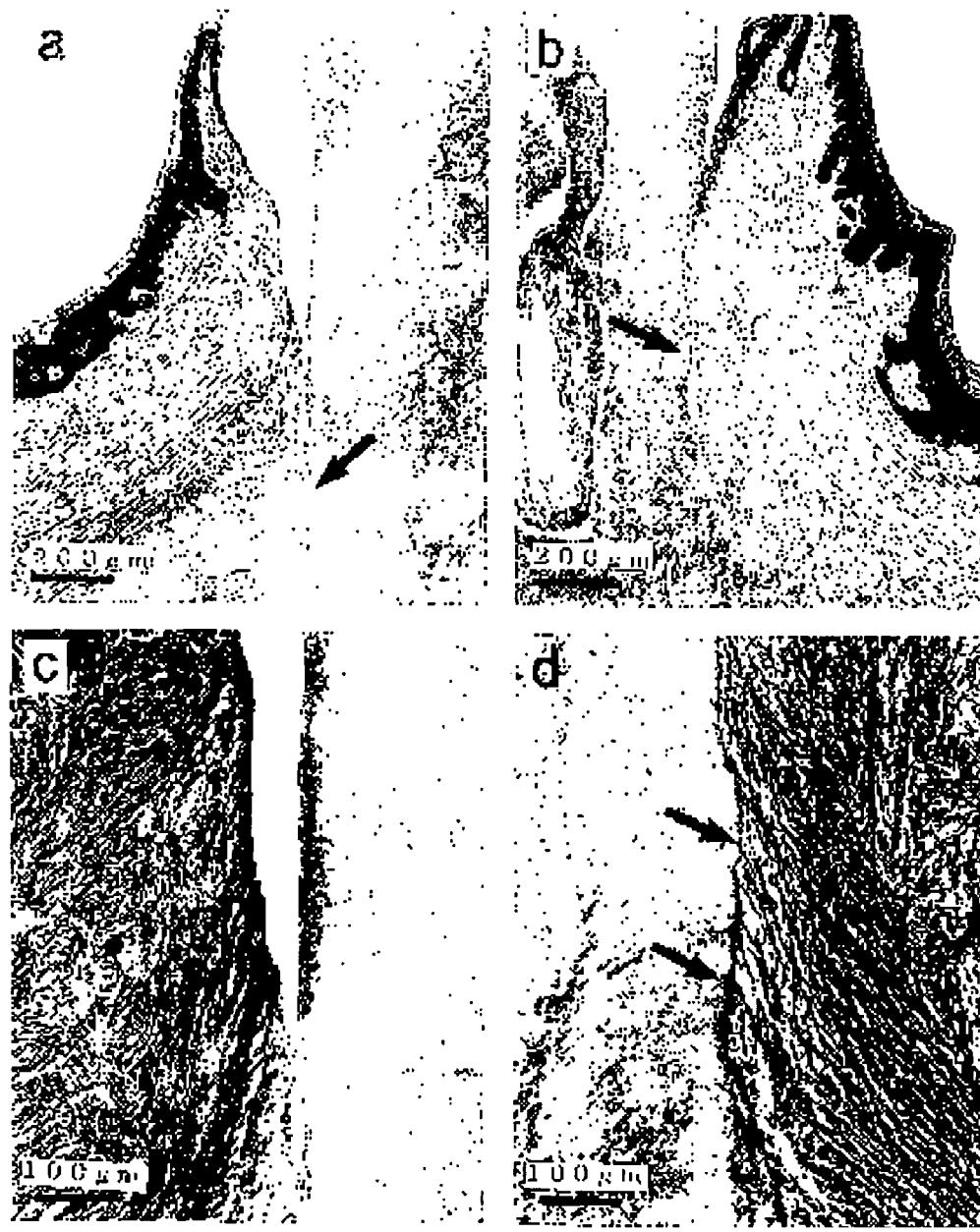
FIG. 9 shows the healing state of periodontal tissues four weeks after the operation shown in Example 5 and Comparative Example 3.

A periodontal tissue defect was prepared in an immunodeficient small animal to try transplantation of the cultured periodontal ligament cell sheet of Example 2 into this defect. Specifically, a bone defect was prepared in the mesial alveolar bone of maxillary molar of an F344 nude rat and the cementum was removed and the dental root dentine was exposed to prepare an experimental periodontal tissue defect. The lower part of the cultured periodontal ligament cell sheet of Example 2 was coated on the above described exposed dentine and the wound surface was protected to complete transplantation. One week and four weeks after the operation, the transplanted site was collected and subjected to formalin immobilization, EDTA-decalcification and paraffin-embedding according to the conventional method, and then continuous slices each having a length of 5 μm were prepared and subjected to H-E staining and the healing process of periodontal tissues was histologically observed with time. The result of the tissue state after one week is shown in FIG. 8 (d: the entire tissue image, d: an enlarged image of the cultured periodontal ligament cell sheet adhering part). As shown in FIG. 8d, it would be understood that the cultured periodontal member cell sheet closely adhered to the dental root dentine. The result of the tissue state four weeks after the operation is shown in FIG. 9 (b: the entire tissue image, d: an enlarged image of the cultured periodontal ligament cell sheet adhering part). As shown in FIG. 9d, it would be understood that the cultured periodontal ligament cell sheet closely adhered to the dental root dentine and was oriented and came to syndesmotic tissues and transplantation of the cultured periodontal ligament cell sheet of this invention enables reconstruction of periodontal tissues.

Comparative Example 3

A bone defect was prepared in the mesial alveolar bone of maxillary molar of an F344 nude rat in the same manner as in Example 5 and the cementum was removed and the dental root dentine was exposed to prepare an experimental periodontal tissue defect. Thereafter, without transplanting the cultured periodontal ligament cell sheet, tissue slices were prepared in the same manner as in Example 5 and the healing process of periodontal tissues was histologically observed with time. The result of the tissue state after one week is shown in FIG. 8 (a: the entire tissue image, c: an enlarged image of the periodontal tissue defect). As shown in FIG. 8c, it would be understood that the periodontal tissue defect remained as it was and healing did not proceed. The result of the tissue state four weeks after the operation is shown in FIG. 9 (a: the entire tissue image, c: an enlarged image of the periodontal tissue defect). As shown in FIG. 9c, it would be understood that the periodontal tissue remained as it was even four weeks after the operation and healing hardly proceeded. This tissue state was clearly different from that of Example 5 in which the cultured periodontal ligament cell sheet of this invention was transplanted.

INDUSTRIAL APPLICABILITY

With high bioadherent regenerative periodontal ligament cell sheet described in this invention, the bioadherence to the dental root would be very high and target cells could be transplanted at a high density to positively reconstruct periodontal tissues. Furthermore, by laminating the cell sheets to be transplanted to allow the cell sheets to possess a three-dimensional polarity, an adhesion apparatus could be more efficiently reconstructed and clinical application thereof to moderate periodontitis, sever periodontitis, gingival recession and the like is highly promising. Thus, the present invention is a very useful invention in the field of biology and the like such as cytoengineering and medical engineering.

The invention claimed is:

1. A laminar structure comprising two or more cultured periodontal ligament cell sheets stacked on top of each other and having a syndesmotic microstructure, wherein the outer side of one of the cell sheets is attached to a polymer-coated culture support and wherein the polymer-coated culture support is removable therefrom.

2. The laminar structure of claim 1, wherein each cell sheet comprises periodontal ligament fibroblasts or a mixture of periodontal ligament fibroblasts and at least one cell selected from the group consisting of cementoblasts, osteoblasts, gingival fibroblasts, and endothelial cells.

3. The laminar structure of claim 2, further comprising on top of the top most sheet of cells a sheet of gingival fibroblasts, on top of the sheet of gingival fibroblasts a sheet of osteoblasts; and below the bottom most sheet of cells a sheet of cementoblasts.

4. The laminar structure of claim 1, wherein the laminar structure is obtained by layering one of the cultured periodontal ligament cell sheets onto another.

5. The laminar structure of claim 1, wherein the laminar structure is obtained by layering a second cultured cell sheet and optionally one or more additional cultured cell sheets onto a first cultured cell sheet, wherein each cell sheet comprises periodontal ligament fibroblasts and optionally one or more cells selected from the group consisting of cementoblasts, osteoblasts, and gingival fibroblasts.

6. The laminar structure of claim 1, wherein the laminar structure is obtained by layering of said cell sheets onto both the upper and lower sides of another layer of said cell sheets.

7. The laminar structure of claim 6, wherein the structure comprises:
   (a) a layer having said upper and lower sides, comprising (i) periodontal ligament fibroblasts or (ii) a mixture of periodontal ligament fibroblasts and at least one cell selected from the group consisting of cementoblasts, osteoblasts, gingival fibroblasts, and endothelial cells;
   (b) a cell sheet composed of osteoblasts layered onto the upper side of (a); and
   (c) a cell sheet composed of cementoblasts layered onto the lower side (a).

8. The laminar structure of claim 1, wherein the cultured periodontal ligament cell sheet is detachable from the culture support without undergoing a protease treatment and wherein linear shrinkage of the cell sheet after said detachment is maintained at 20% or less.

9. The laminar structure of claim 8, wherein the cells of the cultured periodontal ligament cell sheet are detached from the culture support within 21 days after the cells become a confluent culture on the support surface.

10. The laminar structure of claim 1, wherein the laminar structure is useful for partially or entirely treating a damage to or defect of an affected part in periodontal tissues.

11. The laminar structure of claim 10, wherein the treating is performed by placing the laminar structure onto a damaged or defective part of and thereby covering a dental root surface.

12. The laminar structure of claim 10, wherein the treating is performed by placing the lower side of the laminar structure onto a damaged or defective part of and thereby covering a dental root surface.

13. The laminar structure of claim 10, wherein the laminar structure is cuttable to the size and the shape of the affected part upon covering the affected part therewith.

14. The laminar structure of claim 1, wherein the laminar structure is useful for transplanting to treat a damage or defect of an affected part in periodontal tissues.

15. The laminar structure of claim 14, wherein transplanting comprises covering the dental root surface with the cultured periodontal ligament cell sheet.

16. The laminar structure of claim 1, wherein the laminar structure is of sufficient dimensions to be cut to the size of and shaped for treating an affected part of a dental root surface in need thereof.

17. A method of treating a damage or defect of an affected part in a periodontal tissue in need thereof, the method comprising detaching the laminar structure of claim 1 from the culture support, and then transplanting the support-detached laminar structure to cover part or the entirety of said damage or defect.

18. The method of claim 17, wherein transplanting comprises covering the dental root surface with the support-detached laminar structure.

19. The method of claim 18, wherein covering the dental root surface comprises cutting the support-detached laminar structure to the size and the shape of the affected part upon covering the dental root surface therewith.

20. The method of claim 17, wherein the periodontal tissue in need thereof is a tissue in a patient suffering from moderate periodontitis, severe periodontitis, and/or gingival recession.

* * * * *